US008693618B2

(12) United States Patent
Tischenko et al.

(10) Patent No.: US 8,693,618 B2
(45) Date of Patent: Apr. 8, 2014

(54) SCANNER DEVICE AND METHOD FOR COMPUTED TOMOGRAPHY IMAGING

(75) Inventors: Oleg Tischenko, München (DE);
Matthias Klaften, München (DE);
Christoph Hoeschen, Hebertshausen (DE); Martin Hrabe de Angelis, Fahrenzhausen (DE)

(73) Assignee: Helmholtz Zentrum München Deutsches Forschungszentrum für Gesundheit und Umwelt (GmbH) (DE)

( * ) Notice: Subject to any disclaimer, the term of this patent is extended or adjusted under 35 U.S.C. 154(b) by 441 days.

(21) Appl. No.: 12/996,154

(22) PCT Filed: Jun. 5, 2009

(86) PCT No.: PCT/EP2009/004063
§ 371 (c)(1),
(2), (4) Date: Feb. 9, 2011

(87) PCT Pub. No.: WO2009/146937
PCT Pub. Date: Dec. 10, 2009

(65) Prior Publication Data
US 2011/0222648 A1 Sep. 15, 2011

(30) Foreign Application Priority Data
Jun. 6, 2008 (EP) ..................................... 08010393

(51) Int. Cl.
*A61B 6/03* (2006.01)
(52) U.S. Cl.
USPC .................................... 378/4; 378/17; 378/20
(58) Field of Classification Search
USPC ..................... 378/4, 10, 17, 19, 20
See application file for complete search history.

(56) References Cited

U.S. PATENT DOCUMENTS

| 4,149,079 | A | 4/1979 | Ben-Zeev et al. |
| 5,119,408 | A | 6/1992 | Little et al. |
| 2006/0056577 | A1 | 3/2006 | Hunt |
| 2006/0233295 | A1 | 10/2006 | Edic et al. |
| 2007/0116175 | A1 | 5/2007 | Zhang et al. |
| 2008/0272296 | A1* | 11/2008 | Frach et al. ................... 250/306 |

FOREIGN PATENT DOCUMENTS

| JP | 561240145 A | 10/1986 |
| JP | 06-331569 | 12/1994 |
| JP | 2004-301861 | 10/2004 |
| JP | 2006-84467 | 3/2006 |
| RU | 766 264 | 2/1991 |
| WO | 02/056752 | 7/2002 |
| WO | 2006/069708 | 7/2006 |
| WO | 2007/034357 | 3/2007 |

* cited by examiner

Primary Examiner — Glen Kao
(74) Attorney, Agent, or Firm — DLA Piper LLP (US)

(57) ABSTRACT

A scanner device for computed tomography imaging of an object, includes a measurement device including a source device arranged for irradiating the object with at least one beam and a detector device arranged for detecting radiation transmitted through the object, wherein the source device has a fixed position relative the detector device, and a carrier device accommodating the object in a position between the source device and the detector device, wherein the measurement device and the carrier device are capable of a scanning movement relative to each other, and the measurement device and the carrier device have a fixed spatial orientation during the scanning movement. Furthermore, a scanning method for computed tomography imaging of an object is described.

15 Claims, 4 Drawing Sheets

SCANNER DEVICE AND METHOD FOR COMPUTED TOMOGRAPHY IMAGING

RELATED APPLICATIONS

This is a §371 of International Application No. PCT/EP2009/004063, with an international filing date of Jun. 5, 2009 (WO 2009/146937 A1, published Dec. 10, 2009), which is based on European Patent Application No. 08010393.0 filed Jun. 6, 2008 and U.S. Patent Application No. 61/059,436 filed Jun. 6, 2008.

TECHNICAL FIELD

The present disclosure relates to a scanner device for computed tomography (CT) imaging of an object, in particular to a scanner device comprising a measurement device with source and detector devices and a carrier device accommodating the object, wherein the measurement and carrier devices are capable of a scanning movement relative to each other. Furthermore, the present disclosure relates to a scanning method for CT imaging of an object. The scanner device and the scanning method can be used with all applications of CT imaging, in particular in the fields of material sciences, medical examinations, construction technique, techniques concerning security matters or the like.

BACKGROUND

CT imaging is based on an irradiation of the object under investigation through a sample plane from different projection directions with X-rays created with a source device, followed by the reconstruction of the sample plane on the basis of attenuation data measured with a detector device at the different projection directions. Reconstruction of a complete image is based on collecting projection images with projection angles covering at least 180°. The object is arranged on a carrier device. For setting the different projection directions, the combination of the source and detector devices and the carrier device are capable of a scanning movement relative to each other. Various scanning techniques for implementing the scanning movement have been developed in the past.

With the first generation CT scanner, the source device comprises one single pencil beam source and the detector device comprises one single X-ray detector. A so-called rotation-translation-system is obtained with the following procedure. Starting at a particular angle, the source-detector-system is translated linearly across the field of view (FOV), wherein the data over parallel rays across the FOV are acquired for the projection at that particular angle. After completing the translation, the whole system is rotated, and then another translation is used to acquire data of the next projection direction. These steps of translation and rotation are repeated until the complete set of projection directions has been acquired. In the second generation CT scanner, the detector device comprises a linear array of a few detectors, whereas the X-ray tube creates a narrow fan angle X-ray beam. As in the first generation scanner, the scanner of the second generation is a rotation-translation system which however has a reduced number of rotation steps.

A major limitation of the first and the second generation CT scanners is the translation motion because at the end of each translation, the source-detector-system has to be stopped, the whole system has to be rotated and then the translation motion has to be restarted. The construction of fast scanning devices proved very difficult with these CT scanners. Therefore, first and second CT scanners are not used for current CT imaging.

The third CT scanner, as disclosed e.g. in WO 2007/034357 or U.S. Pat. No. 4,149,079, is characterized by a rotation-rotation-system, referring to the rotation of the source and detector devices. A generic third generation CT scanner 100 is schematically illustrated in FIG. 8 (prior art). The conventional CT scanner 100' comprises a measurement device including a source device 20' and a detector device 30' as well as a carrier device 4' accommodating the object 1' under investigation. The source device 20' comprises a single X-ray tube irradiating the object 1' with an X-ray fan beam. The detector device 30' comprises a plurality of detector elements detecting the radiation transmitted through the object 1'. The source and detector devices 20', 30' have a fixed position relative to each other. For setting the various projection directions, the source and detector devices 20', 30' are rotated around the object 1', i.e. the spatial orientation of the measurement device including the source device 20' and the detector device 30' is continuously changed during scanning.

As an essential advantage, the third generation CT scanners are capable of providing essentially shorter scan times. A complete set of attenuation data required for CT image reconstruction can be collected within some milliseconds. However, conveying of signals from the detector elements requires wires from the detector device 30' to a processing computer or the provision of contact rings for data and power transmission. Wiring has the disadvantage that problems may arise from the continuously changing spatial orientation of the measurement device. In particular, a continuous rotation is impossible, while the contact rings may cause mistakes in calibration of the detector signals. As a result, so-called ring artifacts can be created in the reconstruction image. As a further disadvantage, the efficiency of the fan beam geometry of data collected in the scanner of the third generation is computationally lower than that of the parallel beam geometry.

With the fourth generation CT scanner, the detector elements are removed from the rotating system and are placed on a stationary annulus around the object. In this case, the wiring and ring artifact problems of the third generation CT scanner can be avoided. However, the CT scanners of the fourth generation have an essential disadvantage in terms of their high price. This is due to the large number of detector elements required to form a complete ring. Another drawback of the fourth CT scanners may result from a non-homogeneity of the X-ray geometry. The source-detector distance as well as the thickness of the rays may be different for different detector elements. This may result in further imaging artifacts.

Further CT scanner have been proposed, which require mechanic structures being even more complex compared with the third or fourth generation CT scanners. As an example, SU 766 264 A1 discloses a scanning mechanism having a measuring device with one single X ray source and for each object to be measured one single detector element. For collecting data for multiple projection directions, the object is translated and rotated between the source and the detector element, i.e. the spatial orientation of an object carrier is continuously changed during scanning. Further scanners having a rotating object carrier are described in U.S. Pat. No. 5,119,408 A and WO 02/056752 A2.

Contrary to CT imaging, conventional tomosynthesis imaging can be adapted for collecting projections images during a straight translation of the object between the source and the detector element (e.g. US 2007/0116175 A1). However, this covers a limited range of projection angles only, so that a reconstruction of a complete tomographic image is impossible with the tomosynthesis imaging technique.

SUMMARY

In view of the foregoing problems, an objective of this disclosure is to provide an improved scanner device for CT imaging of an object being capable of avoiding the limitations of the conventional scanning techniques. Furthermore, an objective of the disclosure is to provide an improved scanning method for CT imaging. In particular, the improved scanning technique is to be capable of directly implementing a parallel beam geometry while providing short scan times as with the third or fourth generation CT scanners. Furthermore, imaging artifacts are to be avoided with the improved scanning technique.

These objectives are achieved with a scanner device or a scanning method comprising the features disclosed and claimed herein.

According to a first general aspect of the disclosure, a scanner device adapted for CT imaging comprises a measurement device with a source device and a detector device having a fixed position relative to each other and a carrier device being adapted for positioning an object under investigation in a field of view (FOV) between the source device and the detector device, wherein the measurement device and the carrier device are movable relative to each other for performing a scanning movement and wherein the measurement device and the carrier device have a fixed spatial orientation during the scanning movement. The detector device comprises a plurality of detector elements, wherein the detector elements comprise X-ray sensing elements having a single pixel shape or a line or areal shape with multiple pixels.

According to a second general aspect of the disclosure, a scanning method for CT imaging comprises the steps of irradiating an object under investigation with X-rays created with a source device and detecting radiation transmitted through the object along a plurality of different projection directions with a detector device, wherein the projection directions are set with a scanning movement of a carrier device supporting the object and the combination of source and detector devices relative to each other, wherein the source and detector devices and the carrier device have a fixed spatial orientation during the scanning movement.

Advantageously, the disclosed scanner device and scanning method are adapted for collecting attenuation data resembling the parallel beam geometry like with the first or second generation CT scanners. Contrary to these scanner types, the position of the source device and the position of the detector device are fixed in space or, if the source and detector devices are adapted for performing the scanning movement, both are simultaneously moved with the same velocity (direction, amount). As a further advantage, the collection of a data set, which is necessary for the reconstruction of an image plane (slice), can be completed in a time that is comparable to that of the third generation CT scanners or even faster. According to the disclosure and in contrast to the third generation CT scanners, the measurement device with the source and detector devices does not rotate around the carrier device in the conventional way. Both the measurement device and the carrier device have a predetermined orientation in space and relative to each other. They are arranged and moved such that this fixed orientation is kept constant during the scanning movement. Advantageously, this scanning design excludes the calibration errors that are typical for the third generation scanners. Furthermore, in contrast to the third generation CT scanners, each detector element of the detector device has a fixed spatial position relative to the object, i.e. each detector element collects data for a predetermined fixed projection angle. Finally, in contrast to the scanners of the fourth generation, the geometry of the data of the disclosed scanning technique admits homogeneity. Due to the fixed mutual position of the source and detector devices, any changing distance between the source and detector devices is avoided. Furthermore, the collection of a complete data set per slice can be achieved by using only one half of a detector ring or even less.

An essential feature of the disclosure is represented by the fixed position of the source device relative to the detector device and simultaneously the fixed orientation of the measurement device with the source and detector devices and the carrier device. The term "fixed position" refers to the fact that a reference point of the source device, e.g. a support point or a focal spot of an X-ray tube, and a reference point of the detector device, e.g. a position of a predetermined detector element, have constant relative spatial coordinates. In particular, the term "fixed position" covers a first variant, wherein at least one X-ray tube of the source device and the detector elements of the detector device are rigid components, which are immovable, and a second variant, wherein at least one of the source and detector devices has a fixed position but a variable orientation in space. In other words, the source device has a fixed position relative to the detector elements even if the source device comprises one single X-ray tube, which can be axially rotated for directing X-rays towards varying detector elements.

The term "fixed spatial orientation" means that the orientation (angular position) in space is constant for both the measurement device and the carrier device. The spatial orientation is represented by predetermined, e.g. orthogonal reference directions of the device geometry. As an example, the spatial orientation of the measurement device can be represented by a first line connecting a focal spot of the source device with a detector element of the detector device and a second line perpendicular to the first line. Furthermore, the spatial orientation of the carrier device can be represented by a first line perpendicular on a carrying surface of the carrier device and a second line along the carrying surface.

The term "scanning movement" refers to the movement of the measurement device and the carrier device relative to each other, which is designed for setting the different projection directions of the object irradiation. Generally, the scanning movement results in a translation of the carrier device relative to the measurement device along a curved, in particular circular or polygonal path (scanning line). The scanning movement may comprise a plurality of partial translation phases for adjusting certain ranges of projection directions (see below). Generally, the scanning movement or at least one of the partial translation phases is performed along a reference plane including the beam path from the source device to the detector elements.

As a particular advantage, attenuation data collected with the disclosed scanning technique can be used for image reconstruction with conventional reconstruction algorithms. In particular, image reconstruction can be implemented e.g. with the filtered back-projection (FBP) algorithm or the polynomial-based (OPED) algorithm (see WO 2006/069708). It is to be noted that the disclosed scanning technique offers advantages for both the FBP and the OPED algorithms. The FBP algorithm can be essentially accelerated, while the parallel beam geometry obtained with the disclosure is advantageously adapted to the OPED algorithm.

The scanning movement can be adapted to the requirements of a particular application of the disclosed technique. According to a preferred embodiment of the disclosure, the measurement device is fixed, while the carrier device is moved for performing the scanning movement. This embodiment is preferred in particular for imaging of moveable objects, like work pieces, luggage or medical samples. Furthermore, operation and maintenance of the measurement device are facilitated. According to an alternative embodiment, the carrier device with the object under investigation is fixed, while the measurement device performs the scanning movement. This embodiment may have advantages for imaging immovable objects.

According to a further preferred embodiment of the disclosure, the scanning movement is performed along a circular line. With the above embodiments, the carrier device is translated on a circular line in the center of which the source device or the detector device is arranged, or one of the source or detector devices of the measurement device is translated along a circular line, at the center of which the carrier device is arranged. The scanning movement along a circular line has the particular advantage in terms of keeping the distance between the carrier device and the source or detector device constant during the scanning movement or at least during a partial translation phase of the scanning movement. Accordingly, imaging artifacts can be avoided without a further correction of the collected data.

Further preferred embodiments of the disclosure include the size of the angular range being covered by detector elements of the detector device. According to a first variant, the detector elements are arranged along an angular range of at least 180° relative to the source device. As a main advantage, the detector device can be arranged at least along a half ring with the focal spot of the source device being positioned in the center of the half ring. The main advantage of this design is given by the fact that the scanning movement can be conducted by one single translation of the object through the space between the source device and the detector elements of the detector device along the whole angular range of at least 180°. Accordingly, short scan times as with the $3^{rd}$ generation CT scanners or even shorter can be obtained.

According to a second variant, the detector elements are arranged along an angular range less 180° relative to the source device. This design may have advantages for imaging certain regions of an object, in particular if no complete tomographic data set is required. Otherwise, for collecting the complete data set for image reconstruction, the scanning movement may comprise multiple partial translation phases wherein the spatial orientation of at least one of the measurement device and the carrier device is changed after each partial translation phase.

As an example, with detector elements arranged along an angular range 180°/n (n: natural number), n partial translation phases are required with n different orientations of the carrier device with the object for collecting a whole set of projections. In particular, if the angular range is selected between 180° and 90°, the scanning movement comprises a first partial translation phase of the carrier device with a first spatial orientation relative to the measurement device, followed by a step of changing the orientation by an angle, which is equal to the angular range of the detector elements, and a second partial translation phase of the carrier device. Even with this design, scanning is essentially accelerated compared with the CT scanners of the first or second generation.

The disclosed scanning technique can be adapted for collecting attenuation data for two-dimensional or three-dimensional imaging. In the first case, the detector elements preferably comprise a one-dimensional array extending along a curved, in particular circular and/or a polygonal line. As an example, at least one portion of the array may represent a curved line, while at least a second portion represents a polygonal line. For obtaining a two-dimensional image, the detector elements may be arranged as a two-dimensional array. The shape of the array is selected to represent a curved, in particular cylindrical area and/or a polygonal area. Alternatively, three-dimensional images can be obtained by using a one-dimensional array of detector elements and the performance of multiple scanning movements each of which being adapted for collecting attenuation data for a predetermined imaging plane of the object.

Preferably, the detector elements of the detector device are arranged with an equal center-to-center spacing. With this embodiment, advantages in terms of the assignment of the collected attenuation data to equally angled projection directions are obtained.

According to a further advantageous embodiment of the disclosure, a distance between the carrier and the source device can be adjusted. With a reduction of the distance the spatial resolution of attenuation data collection is improved. By increasing the distance, the irradiation is broadened, which may have an advantage in terms of reducing the radiation exposure of the object.

Variability of the distance between the carrier device and the source device allows a two-step imaging procedure. With a first step, a preview scan could be performed with low resolution. After recognizing a certain region of interest within the object, the distance between the carrier and source devices could be reduced for a second imaging step with increased spatial resolution. This two-step-procedure has particular advantages in medical imaging and luggage screening.

According to a further advantageous embodiment of the disclosure, a distance of the carrier device relative to a main irradiation plane of the measurement device is adjusted. The carrier device can be moved perpendicular to the carrier surface thereof. With this movement, the horizontal imaging plane of the object can be set. By repeating the scanning movement with a plurality of carrier device adjustments, a complete data set for a three-dimensional imaging can be collected.

Another advantage of the disclosure results from the variability of the source device design. According to a first variant, the source device comprises one single X-ray tube only, which is adapted for irradiating the object with one single fan beam. The X-ray tube is arranged with a fixed distance from the detector elements, e.g. in the center of a circular line at which the detector elements are arranged. With this embodiment, advantages are obtained in terms of low complexity of the source device and compatibility with conventional X-ray tubes. According to a particularly preferred feature, the X-ray tube generates the fan beam with a fan angle of at least 180°. Accordingly, the complete detector device can be irradiated simultaneously with one single fan beam. If the fan beam has an angle-dependent inhomogeneity, this can be considered in the evaluation of the detector signals. According to an alternative feature, the X-ray tube generates the fan beam with a fan angle below 180°, preferably below 90°, like e.g. below 80°, e.g. in the range of 5° to 10°, in particular in the range of 12° to 65°. With a fan angle below 180°, the X-ray tube is adapted to be axially rotated during the scanning movement. With the axial rotation of the X-ray tube, the fan beam is aligned with the carrier device and the object arranged on the carrier device, while the position of the source device (X-ray tube) relative to the detector device (detector elements) is kept constant.

According to a second variant, the source device may comprise a plurality of beam elements being arranged along a predetermined irradiation line. The beam elements can be adapted for creating fan beams or pencil beams. The irradiation line may have a curved, in particular circular, and/or polygonal shape as mentioned above with regard to the detector device. In this case, the irradiation line is arranged around the detector device. As an example, the detector device with the plurality of detector elements is arranged in the center of a circular irradiation line. This geometry, which is called "inverse geometry" may have advantages for particular applications of the disclosure, e.g. in the field of medical imaging.

According to a further advantageous embodiment of the disclosure, a collimator mask can be arranged between the source device and the object for irradiating the object with multiple beam components. Preferably, the collimator mask is connected with the detector device. Alternatively, the collimator mask can be arranged as a separate structure in the space between the source device and the carrier device. The collimator mask offers particular advantages in terms of reducing the radiation dose applied to the object, e.g. patient, reducing scatter radiation possibly generated at the source device, shielding of detector elements the signals of which can be used for a scatter signal correction, and/or compensating possible adjustment errors of an X ray tube of the source device. Furthermore, the collimator mask can be used for arranging energy filter in the beam path from the source device to the object and/or for adjusting the source device relative to the object using a laser calibration.

DETAILED DESCRIPTION

Embodiments of the disclosure are described in the following with particular reference to the disclosed geometry of a CT scanner and procedural steps of the scanning method for collecting attenuation data for CT imaging. Details of CT devices, in particular control devices, display devices, power supply devices, details of controlling X-ray tubes, detecting X-rays, processing the collected attenuation data and reconstructing a two- or three-dimensional CT image of the object or a certain partial region thereof are not described here as they are known from conventional CT technique.

Figure 7:
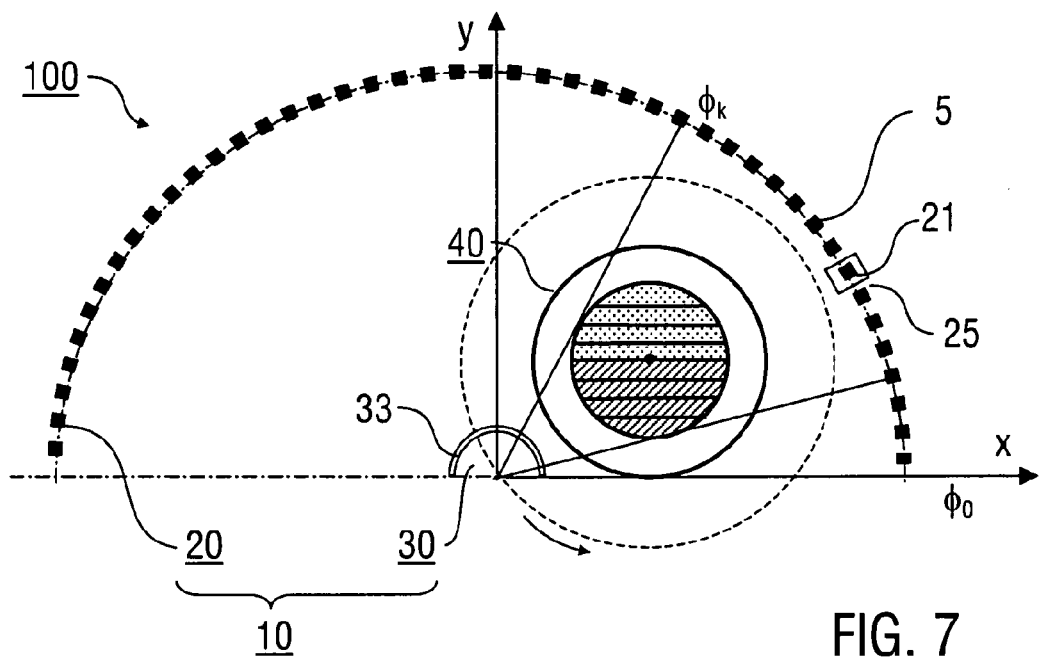
FIG. 7 shows a schematic illustration of another embodiment of the disclosure with a detector device surrounded by the source device ("inverse geometry")
Figure 8:
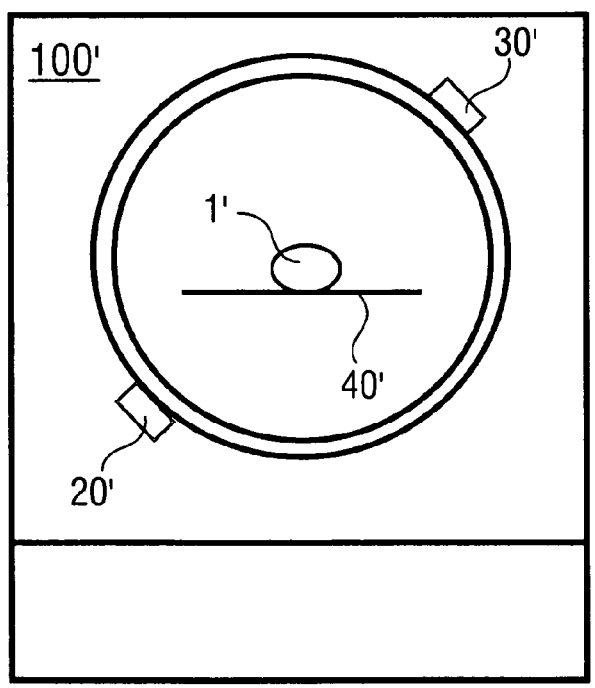
FIG. 8 shows a schematic illustration of a conventional CT scanner device of the third generation (prior art).

Furthermore, the following description of preferred embodiments refers to an arrangement of the detector elements along a semi-circle (FIGS. 1, 2) or a polygonal line (FIG. 5) or the arrangement of fan beam elements along a semi-circle (FIG. 7). It is emphasized that the disclosure is not restricted to these arrangements of the detector or fan beam elements, respectively. As an example, the detector or fan beam elements can be arranged along a full circle or along an angular range below 180°. Furthermore, geometries with curved and/or polygonal sections of the arrangement of detector of fan beam elements can be provided depending on the application of the disclosure.

Figure 1:
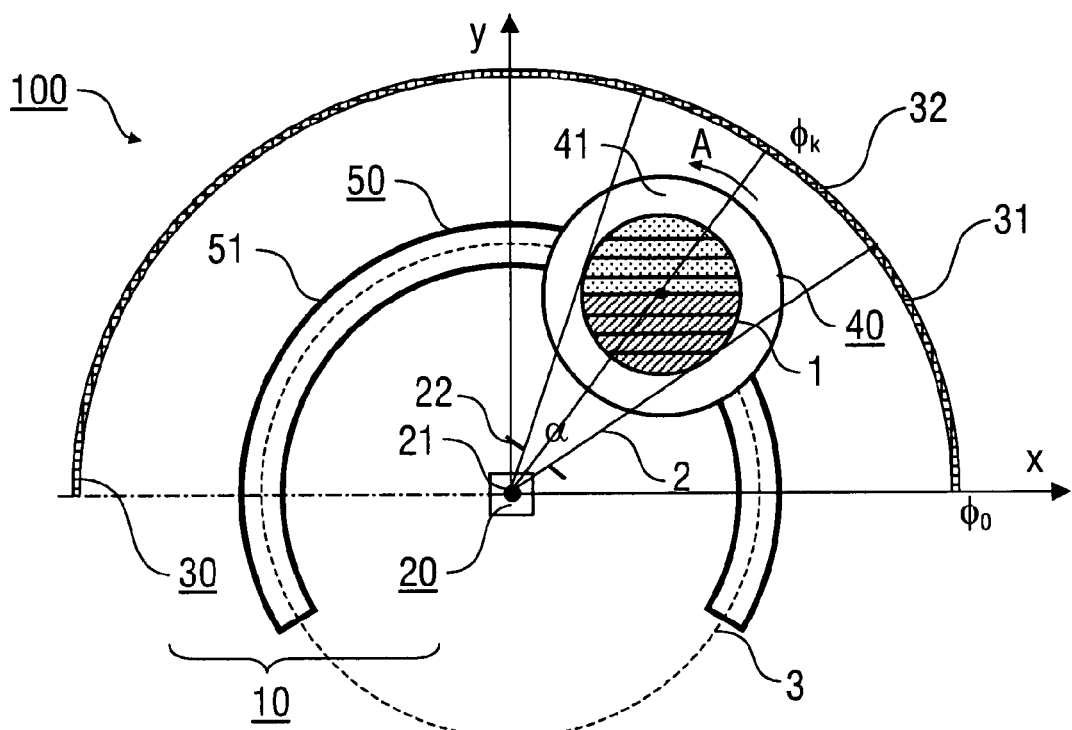
FIGS. 1 and 2 show schematic illustrations of embodiments of the disclosure having a source device surrounded by the detector device.

FIG. 1 schematically illustrates a first embodiment of the disclosed CT scanner device 100 comprising a measurement device 10 with the source device 20 and the detector device 30. Furthermore, the scanner device 100 comprises the carrier device 40, which is movably arranged between the source and detector devices 20, 30. FIG. 1 illustrates an embodiment of the disclosure wherein the measurement device 10 is fixed in space, e.g. in a laboratory or a medical facility, while the carrier device 40 is adapted for performing the scanning movement relative to the measurement device 10. The opposite system, i.e. a scanner with a fixed carrier device and a moveable measurement device is described below with reference to FIG. 2. Furthermore, FIG. 1 illustrates an embodiment of the disclosure, wherein the detector device 30 is arranged along a detector line surrounding the source device 20. The inverse geometry, i.e. a scanner with multiple pencil beam elements arranged along an irradiation line surrounding the detector device is described below with reference to FIG. 7.

The source device 20 comprises an X-ray tube with a focal spot 21 being arranged in the center of the semi-circle detector line of the detector device 30. For simplicity of the description, it is assumed below that the X-ray tube produces a fan beam with a fan angle of 180°. In practice, the fan angle $\alpha$ of the fan beam 2 is typically smaller, e.g. in the range of 12° to 75°. In the first case (180° fan beam) the orientation of the X-ray tube is fixed, while in the second case (fan angle $\alpha$ below 180°), the X-ray tube is axially rotatable for an alignment with the carrier device.

Preferably, the fan angle $\alpha$ of the fan beam 2 produced with the X-ray tube is adjusted such that the complete object 1 under investigation or a certain region of investigation within the object 1 is irradiated during the scanning movement. The source device 20 can be provided with a mask 22 being adapted for adjusting the fan angle. The mask 22 may have advantages for adapting the fan angle to an object with a non-circular cross section. The fan angle can be controlled in dependency on the position of the object during the scanning movement. Furthermore, the mask 22 can be used for adapting the fan angle to the region of interest within the object e.g. if the X-ray beam is to be focussed to a certain part of the object 1. Alternatively or additionally, a collimator mask 23 can be provided as described below with reference to FIGS. 3 and 4.

The detector device 30 comprises a semi-circular one-dimensional array of detector elements 31 or an arrangement of a plurality of single detectors arranged along the semi-circle. Detector elements (or single detectors) can be used as they are known from conventional CT scanner devices, e.g. of the third or fourth generation. The sizes and number of the detector elements is selected in dependency on the requirements of the particular application of the disclosure. As an example, at least 180 detector elements 31, e.g. at least 180 detector elements 31 can be arranged along a semi-circle with a diameter of 20 cm. Depending on the fan angle of the fan beam 2, an arc 32 of detector elements 31 is capable of sensing attenuation values of the radiation transmitted through the object 1. Alternatively, the detector device 30 may comprise a semi-circular two-dimensional array (not shown) of detector elements.

The source device 20 and the detector device 30 are fixedly connected with each other. The distance between the focal spot 21 and the detector elements 31 is selected e.g. in the range of 5 m to 20 cm, preferably in the range of 120 cm to 60 cm. For particular applications, the distance can be even below 5 cm.

Figure 6:
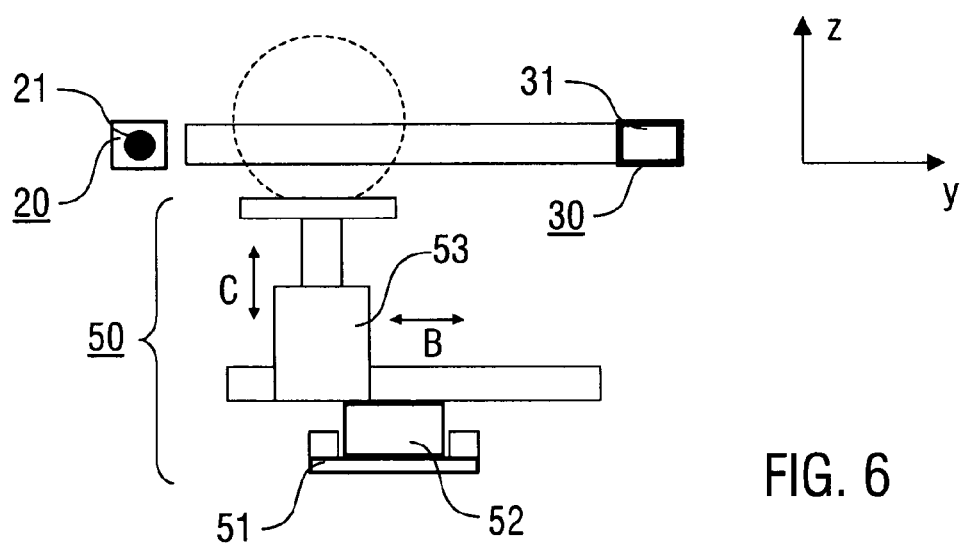
FIG. 6 shows a schematic illustration of a scanner drive device for adjusting the position of the carrier device relative to the measurement device.

The carrier device 40 comprises a platform with a carrier surface 41 (see also FIG. 6). The carrier surface 41 is a plane surface adapted for accommodating the object 1. Fixing devices (not shown) can be provided on the carrier surface 41 for fixing the object 1 as it known from conventional CT scanner techniques. The carrier device 40 is connected with a scanner drive device 50, which generally is adapted for performing the scanning movement of the carrier device (or the measurement device, respectively).

The scanner drive device 50 comprises a guide rail 51 and a drive unit 52 (not shown in FIG. 1, see FIG. 6). The guide rail 51 extends along a scanning line 3, e.g. along a circle. With the drive unit, the carrier device 40 is translated along the guide rail 51. The drive unit comprises e.g. an electrical motor. The scanner drive device 50 is designed such that the carrier device 40 is keeping its initial spatial orientation during the complete scanning movement, e.g. via a platform with two degrees of freedom, each allowing only translation. As the measurement device 10 is spatially fixed, the spatial orientation of the measurement device 10 is kept as well.

For describing the disclosed scanning method, it is assumed that the imaging plane in the object 1 extends in the x-y-plane (aligned e.g. horizontally or vertically) as illustrated in FIG. 1. Accordingly, the projection lines from the focal spot 21 to the detector device 30 are included in the x-y-plane. For aligning the fan beam 2 with the object 1, the X-ray tube of the source device 20 can be axially rotated with the mask 22 with the z-axis being the rotation axis.

The scanning is started e.g. with a position of the carrier device 40 with the object 1 in the positive x-direction relative to the source device 20. The data of the horizontal parallel stripes schematically illustrated in the object 1 are collected by the detector element with the angle $\phi_0$. With the scanning movement, the object 1 is moved along the scanning line 3. In the position depicted in FIG. 1, the projection characterized with $\phi_0$ is completed. At this time, parallel data for the projection associated with the detector element as the angle $\phi_k$ are collected. Every detector element in the detector device 30 collects the parallel data for the projection angle associated with this detector element. In case of a fan angle less than 180°, the scanning process is realized by an alignment of the fan beam of the source device 20 with the position of the object 1.

If the detector elements are spanning an arc less than 180° and a whole set of projections over 180° is to be collected, the scanning movement along the scanning line 3 is divided into multiple partial translation phases, wherein a reorientation of the carrier device takes place between two distinct translation phases. Each of the partial translation phases comprises a complete translation of the carrier device 40 along the guide rail 51. The partial translation phases differ with regard to the orientation of the carrier device 40 relative to the measurement device 10. To this end, the carrier device 40 can be rotated between partial translation phases, e.g. with a position at the positive or negative x-directions.

Figure 2:
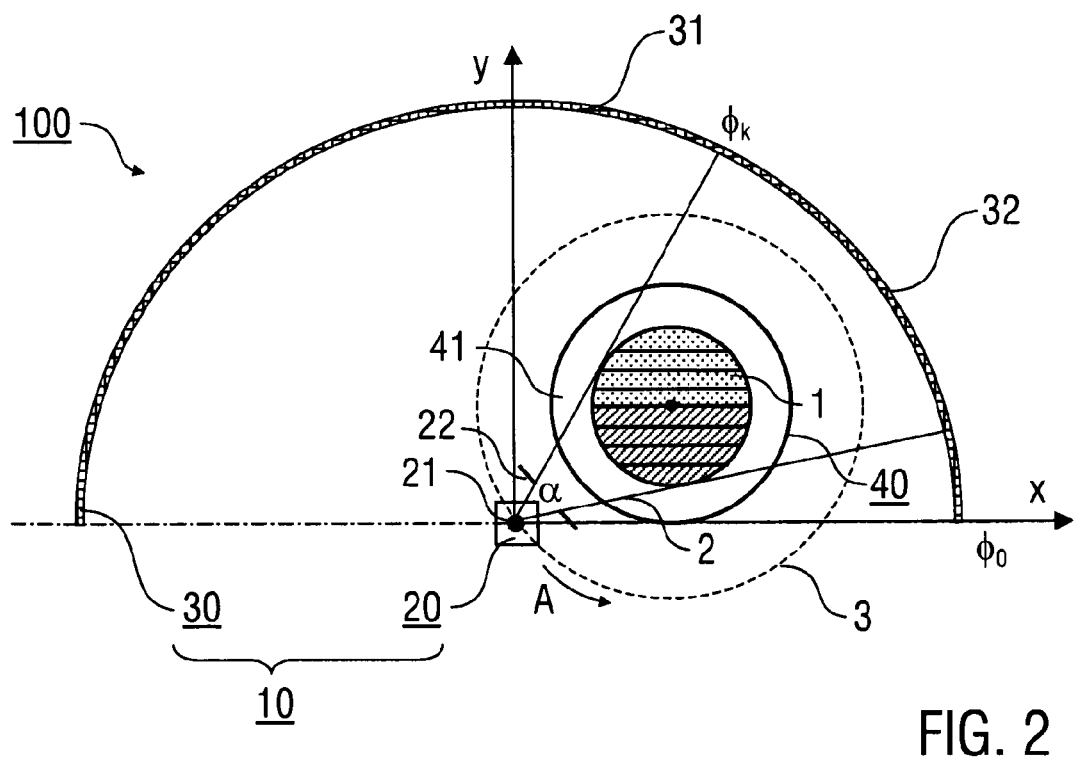

Scanning can be performed also when the measurement device 10 is moved, while the carrier device 40 is fixed (FIG. 2). In this case, the measurement device 10 moves (anticlockwise in FIG. 2) around the fixed carrier device 40 keeping its spatial orientation as described above with reference to FIG. 1. The measurement device 10 is translated with a scanner drive device (not shown) adapted for an operation analogue to the function of the scanner drive device 50 shown in FIGS. 1 and 6. The scanning line 3 (trajectory) of the focal spot 21 is a circle including the object 1. Again, the data of the horizontal parallel stripes are collected by the detector element at the angle $\phi_0$. In case of a fan angle less than 180°, the source device 20 is rotated for aligning the fan beam with the position of the object 1. The whole set of projections over 180° is then completed as soon as the focal spot 21 finishes its translation along the arc of the length 180°+α (α: fan angle).

The scanning movement of the object 1 can be a double rotation as described in the following. The term "double rotation" can be used as the scanning movement can be described as two rotations opposite to each other. The double rotation is provided in contrast to the scanning movement in the second generation CT scanner, which is a combination of a translation and a rotation. With the embodiment of FIG. 2, the focal spot 21 of the source device 20 rotates in counterclockwise direction (see arrow A). This first rotation can be described with the rotation speed $\Omega_1$. Simultaneously, the arc 32 of detector elements 31 is rotating with the focal spot 21 in clockwise direction around the center of the object 1 with a rotation speed $\Omega_2$. The spatial orientation of the arc 32 relative to the object 1 is kept if $\Omega_1 = -\Omega_2$.

Figure 3:
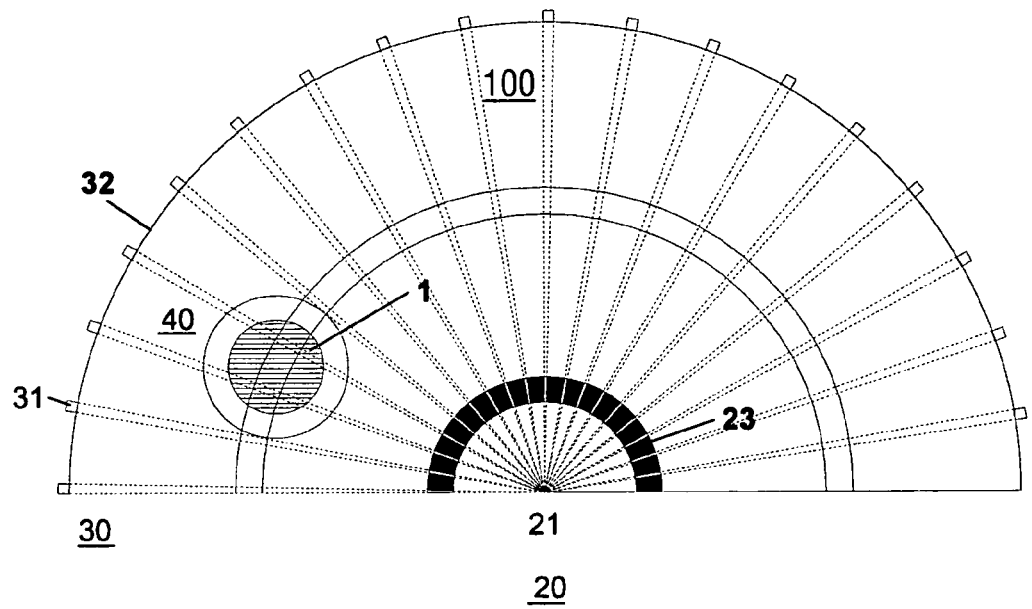
FIGS. 3 and 4 show schematic illustrations of further embodiments of the disclosure having a source device provided with a collimator mask.
Figure 4:
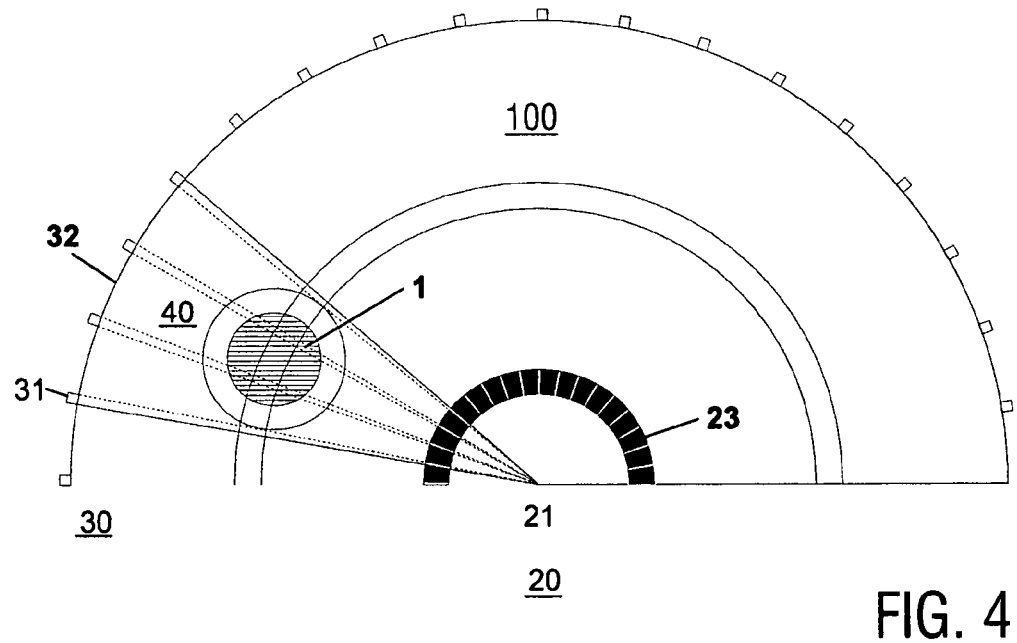

FIGS. 3 and 4 further illustrate the embodiment of FIG. 1, wherein the scanner device 100 is provided with a collimator mask 23. In this case, the detector device 30 comprises detector elements 31, which are arranged with distances along the arc 32. The collimator mask 23 is arranged between the source device 20 and the object 1 on the carrier device 40 for shaping the fan beam emitted from the focal spot 21 of the source device 20 with a plurality of fan beam components 24. The collimator mask 23 comprises a curved, e.g. spherical sheet of shielding material, having a thickness of e.g. 4 mm and including e.g. 180 mask openings for 180 detector elements (each collecting projection data for an angle of 1°). The number, diameter and distribution of the mask openings are selected for providing one beam component for each of the detector elements 31.

The collimator mask 23 may cover 180° for creating the beam components being directed to all of the detector elements, while the source device may emit a 180° fan beam (FIG. 3) or a fan beam having a smaller fan angle (FIG. 4). In the latter case, when the source device 20 may be axially rotated during the scanning movement, a collimator mask covering an angle interval below 180° can be used to cover detector elements currently outside of the fan angle of the source device 20. Preferably, the collimator mask is fixed and aligned relative to the detector device.

The combination of the collimator mask 23 with the discrete arrangement of detector elements 31 has the advantage of reducing the dose in angular regions where no projection data are collected. Alternatively, the collimator mask 23 can be used with an array of detector elements 31, wherein detector elements 31 not irradiated are used for a scatter correction.

Figure 5:
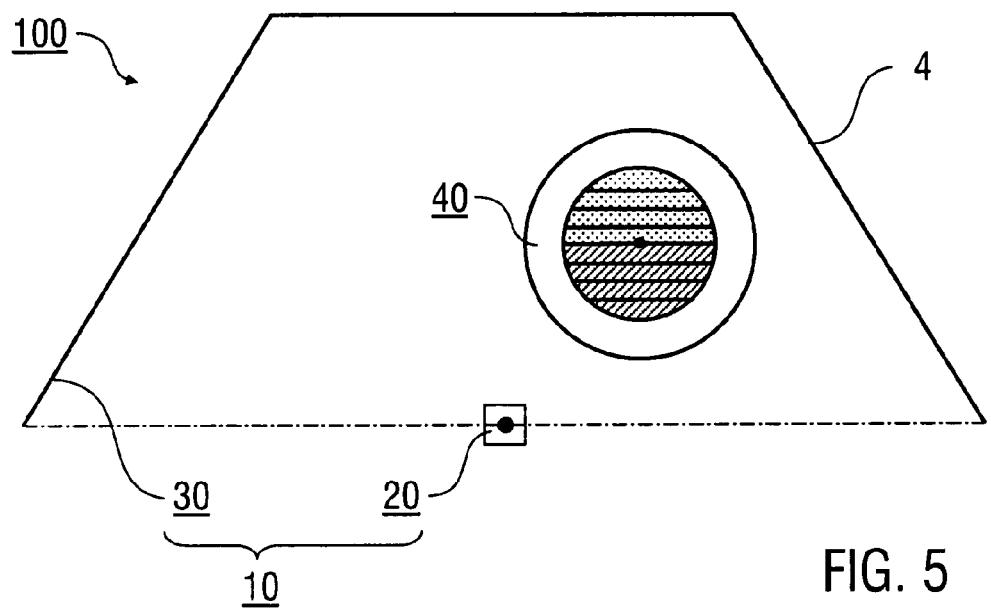
FIG. 5 shows a schematic illustration of another embodiment of the disclosure having a source device surrounded by the detector device.

FIG. 5 illustrates another embodiment of the disclosed scanner device 100 comprising the measurement device 10 with the source device 20 and the detector device 30 and further comprising the carrier device 40. One of the measurement device 10 and the carrier device 40 can be moved with a scanner drive device (not shown). FIG. 5 illustrates that the detector device 30 is not necessarily arranged along a curved detector line 4. With the illustrated example, detector elements 31 are arranged along a polygonal line comprising a plurality of straight sections. The carrier device 40 can be moved along a circular or otherwise curved, e.g. polygonal line. The geometry of FIG. 5 is more complicate compared with the embodiments of FIG. 1 or 2 as the parallel projections are no more equally spaced over the scanning range 180°. However, the geometry of FIG. 5 may have advantages for particular applications of the disclosure, for example for imaging work pieces or other subject, like luggage.

The detector device 30 may comprise multiple X-ray cameras or flat panel detectors arranged along the detector line. Alternatively, multiple detector pixels can be arranged in vertical direction for each projection angle, so that a multi-layer scanner is obtained. As an example, line-shaped detector elements can be oriented perpendicularly to the scanning plane.

FIG. 6 schematically illustrates features of the scanner drive device 50, which is provided for implementing the scanning movement and/or for further adjustments of the object 1. The scanner drive device 50 is shown in a schematic cross-sectional view of scanner device 100 perpendicular to the x-direction. In particular, the scanner drive device 50 can be used for adjusting the distance of the object 1 from the focal spot 21 of the source device 20 and the imaging plane (z-direction) to be irradiated during the scanning movement.

The scanner drive device 50 comprises a guide rail 51 (see FIG. 1), a drive unit 52 for moving the carrier device 40 along the guide rail 51, and an adjustment unit 53 for moving the carrier device 40 in radial direction and/or in z-direction (see arrows B, C).

FIG. 7 illustrates another embodiment of the disclosed scanner device 100 representing the so-called inverse geometry. The scanner device 100 comprises the measurement device 10 with the source device 20 and the detector device 30. Furthermore, the scanner device 100 comprises the carrier device 40. In contrast to the embodiments described above, the source device 20 comprises a plurality of focal spots 21 arranged along a curved, in particular circular, or polygonal irradiation line 5. As an example, the source device 20 comprises a plurality of narrow beam elements 25 each of which having a separate focal point 21. The beam elements 25 create small angle fan beams, with a fan angle approximating a pencil geometry, or pencil beams (two beams illustrated by example). Providing pencil beams may have advantages in terms of obtaining an irradiation geometry being equal to the geometry of the above embodiments of FIGS. 1 to 5. Alternatively, the source device 20 may comprise a common X-ray tube with an anode extending along the semi-circle irradiation line 5. The focal spots 21 are created with an appropriate control of a cathode in the X-ray tube.

The detector device 30 comprises a single detector element or an array 33 of detector elements (as illustrated). Providing a single detector element may have advantages in terms of a reduced complexity of the scanner structure. Using an array of detector elements may have advantages for the collection of attenuation data with high speed.

The scanning movement of the carrier device 40 relative to the measurement device 10 (or: of the measurement device 10 relative to the carrier device 40) is performed as described above with regard to the embodiments of FIGS. 1 to 5.

The features of the device and method disclosed in the above description, the drawings and the claims can be of significance both individually as well as in combination for the realisation of the disclosure in its various embodiments.

The foregoing examples are provided merely for the purpose of explanation and are in no way to be construed as limiting. While reference to various embodiments are shown, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods and uses, such as are within the scope of the appended claims.

The invention claimed is:

1. A scanner device adapted for computed tomography imaging of an object, comprising:
    a measurement device including an X-ray source device arranged for irradiating the object with at least one X-ray beam and a detector device arranged for detecting X-ray radiation transmitted through the object, wherein the X-ray source device has a fixed position relative the detector device such that a reference point of the X-ray source device and a reference point of the detector device have constant relative spatial coordinates; and
    a carrier device accommodating the object in a position between the X-ray source device and the detector device, wherein:
    the measurement device and the carrier device are capable of a scanning movement relative to each other along a curved path in a scanning movement plane that includes any beam path from the X-ray source device to the detector device,
    the carrier device is in a fixed position in space during the scanning movement,
    the measurement device is movable relative to the carrier device,
    the measurement device and the carrier device have a fixed orientation in space, such that reference directions of a device geometry are constant for both the measurement device and the carrier device during the scanning movement,
    the measurement device is movable such that a distance between the X-ray source device and the carrier device can be adjusted, and
    the carrier device is movable such that a perpendicular distance of the carrier device relative to the scanning movement plane can be adjusted.

2. The scanner device according to claim 1, wherein the measurement device is arranged such that the scanning movement is performed along a circular line including the carrier device, wherein at least one of the X-ray source device and the detector device is moved along the circular line, and wherein the carrier device is arranged at a center of a circle defined by the circular line.

3. The scanner device according to claim 1, wherein the detector device comprises a plurality of X-ray detector elements and wherein
    the X-ray detector elements are arranged along an angular range being equal to or larger than 180° relative to the X-ray source device.

4. The scanner device according to claim 1, wherein the X-ray detector elements are arranged as at least one of
    a one-dimensional array along at least one of a curved line and a polygonal line,
    a two-dimensional array along at least one of a curved area and a polygonal area, and
    with equal centre-to-centre spacing.

5. The Scanner device according to claim 1, wherein the X-ray source device comprises one single X-ray tube for irradiating the object with one single fan beam.

6. The scanner device according to claim 5, wherein the X-ray tube is capable of generating the fan beam with a fan angle being equal to or larger than 180°, or
    the X-ray tube is capable of generating the fan beam with a fan angle being less than 180° and the X-ray tube is adapted to be axially rotated so that the fan beam is aligned with the carrier device during the scanning movement.

7. The scanner device according to claim 1, wherein the X-ray source device has a plurality of X-ray beam elements being capable of generating a plurality of fan or pencil beams and wherein the X-ray beam elements are arranged along an angular range being equal to or larger than 180° relative to the detector device.

8. The scanner device according to claim 1, wherein a collimator mask is arranged between the X-ray source device and the carrier device for irradiating the object with multiple X-ray beam components.

9. A scanning method for computed tomography imaging of an object, comprising the steps of:

providing the object on a carrier device in a measurement device between an X-ray source device and a detector device, wherein the X-ray source device has a fixed position relative the detector device, such that a reference point of the X-ray source device and a reference point of the detector device have constant relative spatial coordinates;

irradiating the object with at least one X-ray beam created with the X-ray source device, detecting X-ray radiation transmitted through the object with the detector device, and conducting a scanning movement of the measurement device and the carrier device relative to each other along a curved path in a scanning movement plane that includes any beam path from the X-ray source device to the detector device, wherein the irradiating and detecting steps are repeated with a plurality of different projections angles of the beam relative to the object, wherein:

the carrier device is in a fixed position in space during the scanning movement, the measurement device is moved relative to the carrier device, an orientation of the measurement device and the carrier device is fixed in space, such that reference directions of a device geometry are constant for both the measurement device and the carrier device during the scanning movement, a distance between the X-ray source device and the carrier device is adjusted by moving the measurement device, and a perpendicular distance of the carrier device relative to the scanning movement plane is adjusted by moving the carrier device.

10. A scanning method according to claim 9, wherein the scanning movement is performed along a circular line including the carrier device, wherein at least one of the X-ray source device and the detector device is moved along the circular line, and wherein the carrier device is arranged at a center of a circle defined by the circular line.

11. A scanning method according to claim 9, wherein the detector device comprises a plurality of X-ray detector elements and wherein the X-ray detector elements are arranged along an angular range being equal to or larger than 180° relative to the X-ray source device and the scanning movement comprises one single movement of the measurement device relative to the carrier device covering said angular range.

12. A scanning method according to claim 9, wherein the X-ray source device comprises one single X-ray tube and the object is irradiated with one single fan beam.

13. A scanning method according to claim 12, wherein the X-ray tube is capable of generating the fan beam with a fan angle being equal to or larger than 180°, or the X-ray tube is capable of generating the fan beam with a fan angle being less than 180° and the X-ray tube is axially rotated so that the fan beam is aligned with the carrier device during the scanning movement.

14. A scanning method according to claim 9, wherein the X-ray source device has a plurality of X-ray beam elements being capable of generating a plurality of fan or pencil beams and wherein the X-ray beam elements are arranged along an angular range being equal to or larger than 180° relative to the detector device.

15. A scanning method according to claim 9, comprising the step of irradiating the object with multiple X-ray beam components formed with a collimator mask arranged between the X-ray source device and the carrier device.

* * * * *